US012797584B2

(12) United States Patent
Jeong et al.

(10) Patent No.: US 12,797,584 B2
(45) Date of Patent: Nov. 17, 2026

(54) BODY TEMPERATURE-RESPONSIVE, STIFFNESS-VARYING AND NON-REUSABLE INTRAVENOUS NEEDLE WITH ON-SITE TEMPERATURE SENSING FOR IMPROVED PATIENT CARE, INTRAVENOUS INFUSION SET HAVING THE SAME, AND MANUFACTURING METHOD OF THE SAME

(71) Applicant: Korea Advanced Institute Of Science And Technology, Daejeon (KR)

(72) Inventors: Jae-Woong Jeong, Daejeon (KR); Karen-Christian Agno, Daejeon (KR); Won-il Jeong, Daejeon (KR); Keungmo Yang, Daejeon (KR)

(73) Assignee: Korea Advanced Institute Of Science And Technology, Daejeon (KR)

( * ) Notice: Subject to any disclaimer, the term of this patent is extended or adjusted under 35 U.S.C. 154(b) by 483 days.

(21) Appl. No.: 18/510,950

(22) Filed: Nov. 16, 2023

(65) Prior Publication Data

US 2024/0335640 A1 Oct. 10, 2024

(30) Foreign Application Priority Data

Apr. 10, 2023 (KR) ........................ 10-2023-0046636
Jun. 15, 2023 (KR) ........................ 10-2023-0076657

(51) Int. Cl.
*A61M 25/06* (2006.01)
*A61M 25/00* (2006.01)

(52) U.S. Cl.
CPC .... *A61M 25/0606* (2013.01); *A61M 25/0043* (2013.01); *A61M 2025/0064* (2013.01); *A61M 2207/10* (2013.01)

(58) Field of Classification Search
CPC .................. A61M 25/0043; A61M 2025/0064
See application file for complete search history.

(56) References Cited

U.S. PATENT DOCUMENTS

| | | | | |
|---|---|---|---|---|
| 5,911,711 | A | 6/1999 | Pelkey | |
| 6,383,144 | B1 | 5/2002 | Mooney | |
| 2006/0030824 | A1* | 2/2006 | Hunn | A61M 5/158 604/264 |
| 2006/0173449 | A1* | 8/2006 | Sharareh | A61B 18/1492 606/41 |

FOREIGN PATENT DOCUMENTS

| | | | |
|---|---|---|---|
| EP | 2944269 | A1 | 11/2015 |
| JP | 2000024108 | A | 1/2000 |
| JP | 2006514873 | A | 5/2006 |
| JP | 2008023349 | A | 2/2008 |
| KR | 1020220068573 | A | 5/2022 |

* cited by examiner

*Primary Examiner* — Bradley J Osinski
(74) *Attorney, Agent, or Firm* — NIXON PEABODY LLP

(57) ABSTRACT

Provided are a body temperature-responsive and non-reusable stiffness-varying intravenous (IV) needle with an on-site temperature sensing function, an IV infusion set having the same, and a manufacturing method thereof. The stiffness-varying IV needle may include a body member implemented in a hollow elongated shape through which drug passes and having a variable stiffness according to ambient temperature; and a coating member configured to cover the outer surface of the body member and having biocompatibility.

11 Claims, 10 Drawing Sheets

(a)

(b)

(a)

(b)

BODY TEMPERATURE-RESPONSIVE, STIFFNESS-VARYING AND NON-REUSABLE INTRAVENOUS NEEDLE WITH ON-SITE TEMPERATURE SENSING FOR IMPROVED PATIENT CARE, INTRAVENOUS INFUSION SET HAVING THE SAME, AND MANUFACTURING METHOD OF THE SAME

CROSS-REFERENCE TO RELATED APPLICATION(S)

This application claims the priority benefit of Korean Patent Application Nos. 10-2023-0046636, filed on Apr. 10, 2023, and 10-2023-0076657, filed on Jun. 15, 2023 in the Korean Intellectual Property Office, the disclosure of which is incorporated herein by reference in their entireties.

BACKGROUND

1. Field of the Invention

Example embodiments relate to a body temperature-responsive and non-reusable stiffness-varying intravenous (IV) needle with an on-site temperature sensing function, an IV infusion set having the same, and a manufacturing method thereof.

2. Description of the Related Art

Intravenous (IV) administration refers to an injection method of directly injecting therapeutic drug into the vein using a needle. Since the drug is directly administered into the blood vessel, absorption time is short and a large amount of drug can be injected into a patient over a long period of time. Such aforementioned characteristics made the IV infusion an important medical method that may be easily applied and widely performed in an emergency situation, when administration through other routes halves the effect of the drug, or when administration of the drug through the skin or muscles causes side effects to patients.

IV medication is performed over several hours to several days depending on a patient's condition after inserting a needle into the patient's vein. There are two types of needles that are currently being used in administering an IV in hospitals. The first type is a butterfly needle. This allows effective drug delivery with a short metal needle, but limits the patient's movement. The second type is an over-the-needle IV catheter. This is in a form of a plastic tube and is inserted into the vein using an assisted metal needle made up of stainless steel. Although the second type has a disadvantage in terms of cost, the over-the-needle IV catheter is bendable along the direction of the blood vessel after being inserted in the blood vessel and thus, is relatively advantageous compared to the butterfly needle in terms of the patient's movement. However, since the over-the-needle IV catheter is made of a more rigid material than the blood vessel, a risk of damage to the blood vessel wall still remains.

The above IV access devices may be easily inserted into the blood vessel, but are manufactured in a rigid form, causing a large gap in mechanical property with the soft biological tissue, which may cause various issues for the patient and medical personnel. One issue is that a mismatch in mechanical property between a rigid IV access device and the soft tissue may damage a thin blood vessel wall at an IV infusion site when the patient moves, further leading to tissue inflammation, needle blockage, or drug leakage caused by movement of the indwelling IV access device. Due to this issue, the patient's free movement during IV infusion is greatly restricted and, in many cases, replacement and re-siting of the rigid IV catheter, for instance, needs to be performed every 72 to 96 hours to prevent issues, such as inflammation. Another issue is that a rigid needle may threaten the safety of medical personnel handling the injection. Needle stick injuries among healthcare providers frequently occur and when such accidents occur, special caution is required as there is a risk of infection due to the transmission of deadly virus such as human immunodeficiency virus (HIV) or hepatis B/C through the patient's blood. Because of this risk, the World Health Organization (WHO) emphasized the need for non-reusable needles. Accordingly, syringes with a safety function are developed. However, even in this design, needles still remain in a rigid form and thus, the risk of needle-related incidents still remains.

SUMMARY

Example embodiments provide a disposable stiffness-varying intravenous (IV) needle that converts from a rigid form to a soft form by body temperature to improve bio-tissue affinity, is non-reusable, and has an on-site temperature sensing function.

Also, example embodiments provide a method of manufacturing the stiffness-varying IV needle.

According to at least one example embodiment, there is provided a stiffness-varying IV needle including a body member implemented in a hollow elongated shape through which drug passes and having a variable stiffness according to body temperature; and a coating member configured to cover the outer and inner surface of the body member and having biocompatibility.

According to at least one example embodiment, there is provided an IV infusion set including a stiffness-varying IV needle; a tube through which drug is supplied; and a hub fastened between the stiffness-varying IV needle and the tube and configured to allow the stiffness-varying IV needle and the tube to communicate and to provide the drug supplied through the tube to the stiffness-varying IV needle, wherein the stiffness-varying IV needle includes a body member implemented in a hollow elongated shape through which the drug passes and having a variable stiffness according to body temperature; and a coating member configured to cover the outer and inner surface of the body member and having biocompatibility.

According to at least one example embodiment, there is provided a method of manufacturing a stiffness-varying IV needle, the method including manufacturing a body member having a variable stiffness according to body temperature to be implemented in a hollow elongated shape through which drug passes; and forming a coating member having biocompatibility to cover the outer and inner surface of the body member.

According to some example embodiments, a stiffness-varying IV needle may be maintained in a rigid form at room temperature after being manufactured due to its variable stiffness and may be inserted into a patient's vein and, after insertion into the vein, may convert to a soft form in the body temperature range and may conform to a vein deformation that occurs while the patient moves. Therefore, the stiffness-varying IV needle may continue to stably inject a drug without damaging the blood vessel wall while being inserted into the patient' vein. Here, since the stiffness-varying IV needle irreversibly converts into soft mode within body temperature range and is maintained in the soft form at room temperature even after exiting the patient's vein, reusing the same needle is impossible and this makes it possible to prevent an accident, such as medical staff being sticked by the stiffness-varying IV needle.

Also, according to some example embodiments, since a stiffness-varying IV needle has an embedded temperature sensor, the temperature sensor may be used to monitor a patient's core body temperature while the stiffness-varying IV needle is inserted into the patient's vein. Conversely, the temperature sensor may be used to detect undesired drug leakage that may occur when the stiffness-varying IV needle is inserted at an erroneous location within the soft biological tissue. In this manner, the temperature sensor does not necessitate a medical device required to monitor the patient's condition or a drug injection state and enables a better medical service to be provided to the patient.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION

Hereinafter, example embodiments will be described with reference to the accompanying drawings.

Figure 1:
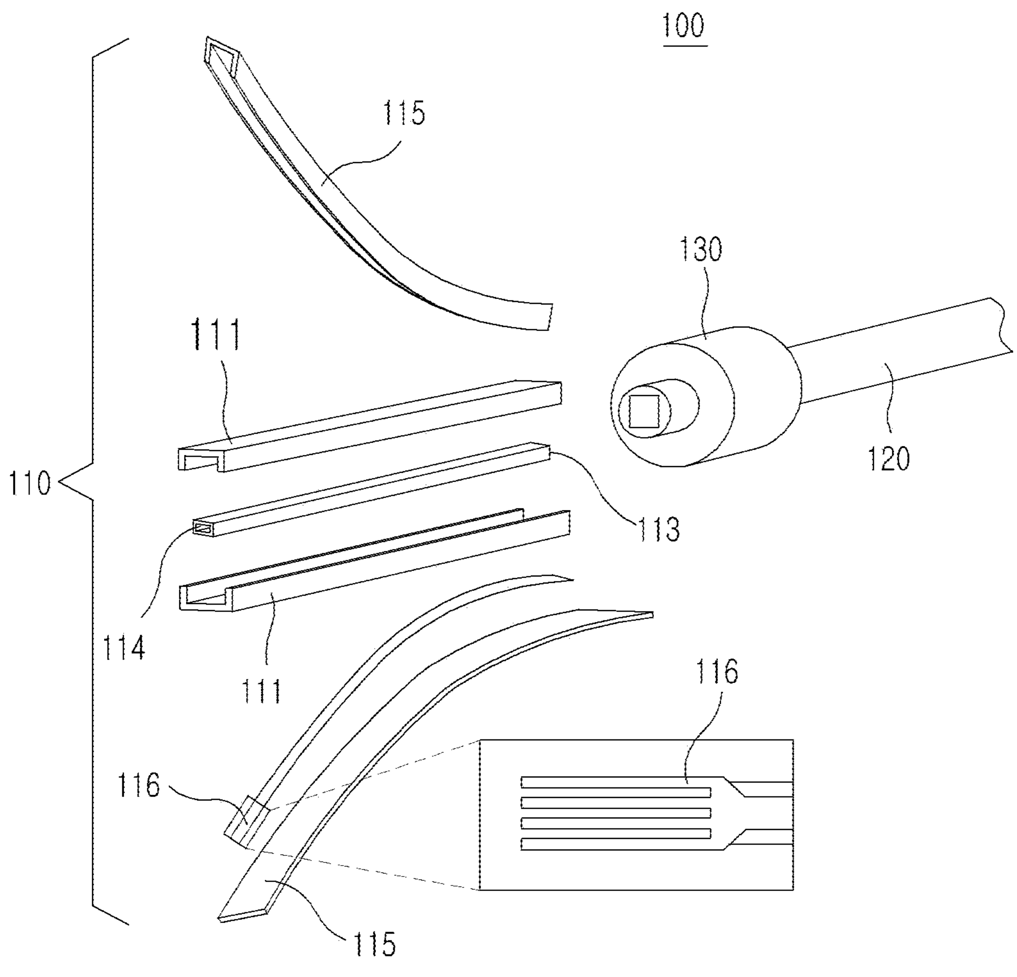
FIG. 1 is an exploded perspective view showing a stiffness-varying intravenous (IV) infusion set according to various example embodiments.
Figure 2A:
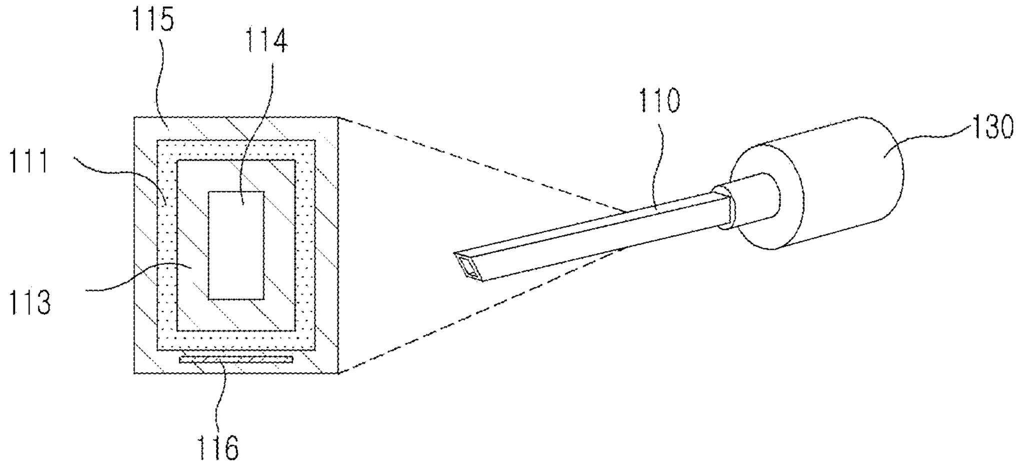
FIG. 2A illustrates a stiffness-varying IV needle in a rigid form and a cross section of the stiffness-varying IV needle according to various example embodiments.
Figure 2B:
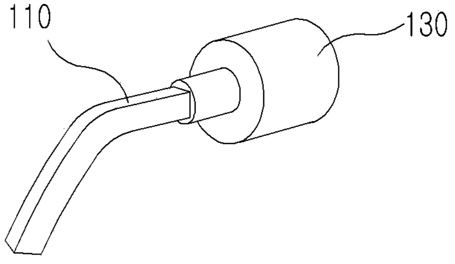
FIG. 2B illustrates a stiffness-varying IV needle in a soft form according to various example embodiments.
Figure 3:
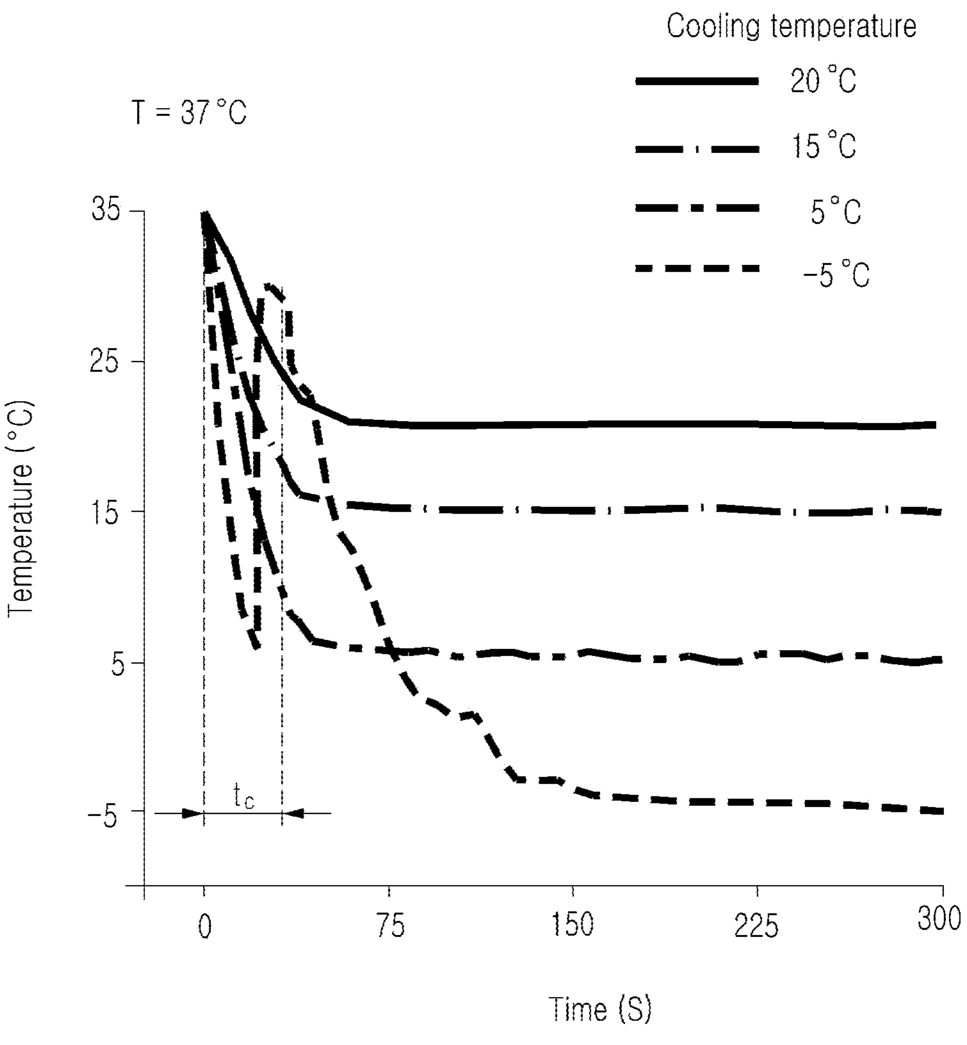
FIG. 3 is a graph explaining irreversibility of an example of a body member at room temperature of FIG. 1 after needle injection.
Figure 4:
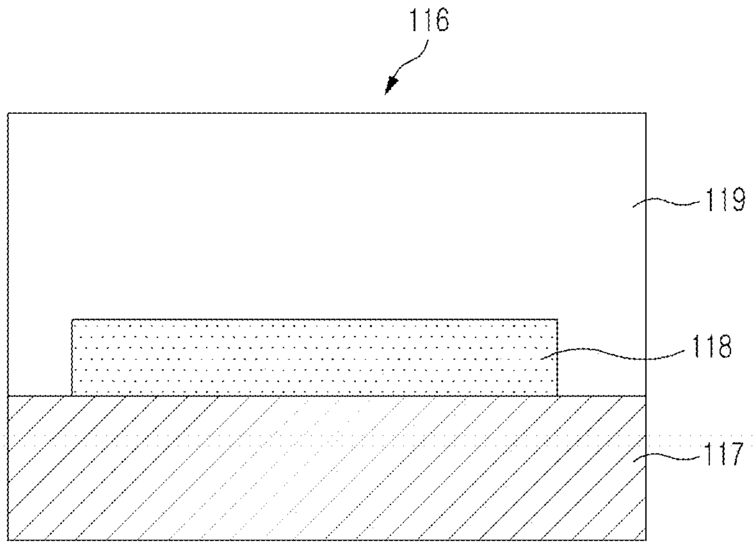
FIG. 4 illustrates a cross section of an example of a body sensor of FIG. 1.
Figure 4:
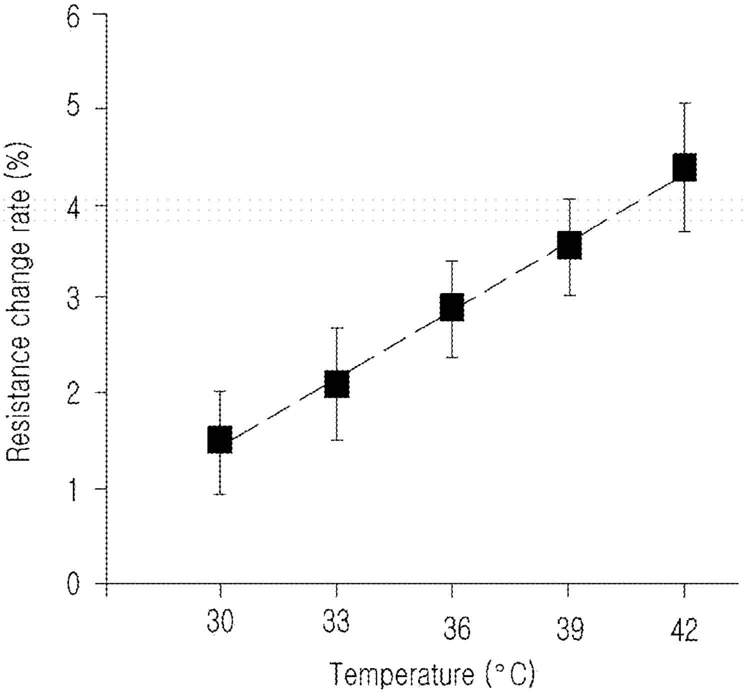

FIG. 1 is an exploded perspective view showing a stiffness-varying intravenous (IV) infusion set 100 according to various example embodiments. FIGS. 2A and 2B illustrate examples of explaining characteristics of a stiffness-varying IV needle 110 according to various example embodiments. FIG. 2A illustrates the stiffness-varying IV needle 110 in a rigid form and a cross section of the stiffness-varying IV needle 110. FIG. 2B illustrates the stiffness-varying IV needle 110 in a soft form according to various example embodiments. FIG. 3 is a graph explaining irreversibility of an example of a body member 111 at room temperature after injection of FIG. 1. FIG. 4 illustrates a cross section of an example of a body sensor 116 of FIG. 1.

Referring to FIGS. 1, 2A, and 2B, the IV infusion set 100 may be used to inject drug into a patient' vein and may include the stiffness-varying IV needle 110, a tube 120, and a hub 130. The stiffness-varying IV needle 110 may be inserted into the patient's vein. The tube 120 may supply the drug to be injected into the patient's vein through the stiffness-varying IV needle 110. The hub 130 may be fastened between the stiffness-varying IV needle 110 and the tube 120 and may allow the stiffness-varying IV needle 110 and the tube 120 to communicate. Accordingly, the hub 130 may provide the drug supplied through the tube 120 to the stiffness-varying IV needle 110, and the drug may be injected into the patient' vein through the stiffness-varying IV needle 110.

According to various example embodiments, the stiffness-varying IV needle 110 may include at least one of the body member 111, a channel 113, a coating member 115, and the temperature sensor 116. In some example embodiments, at least one of the components of the stiffness-varying IV needle 110, for example, the channel 113 or the temperature sensor 116, may be omitted. In some example embodiments, at least one component may be added to the stiffness-varying IV needle 110.

The body member 111 may be implemented in a hollow elongated shape through which the drug passes. In some example embodiments, the body member 111 may have a square or circular cross-sectional outline shape. The body member 111 may have a variable stiffness according to ambient temperature. That is, the body member 111 may have a stiffness that may vary in response to the body temperature.

In detail, the body member 111 may be manufactured with a stiffness for maintaining a predefined shape at temperature below a body temperature range and may be maintained at that stiffness while the ambient temperature is below the body temperature range. Therefore, as illustrated in FIG. 2A, the stiffness-varying IV needle 110 may be maintained in a rigid form at room temperature, for example, at approximately 25 degrees and thus, may be inserted into the patient's vein. If the body member 111 is exposed to an ambient temperature equal to body temperature, at approximately 37 degrees Celsius, the body member 111 may irreversibly change to have a lower stiffness than the corresponding stiffness and become flexible, making the shape deformable. Therefore, as illustrated in FIG. 2B, after being inserted into the patient's vein, the stiffness-varying IV needle 110 may be maintained in a soft form in the body temperature range, for example, at approximately 37 degrees Celsius and thus, may be deformable along the patient's vein during indwelling use. Also, if the temperature to which the body member 111 is exposed to changes to be greater than or equal to the body temperature range, the body member 111 may be maintained at a low stiffness without returning to an original stiffness although the ambient temperature changes back to be below the body temperature range. Therefore, as illustrated in FIG. 2B, the stiffness-varying IV needle 110 may be maintained in the soft form at room temperature, for example, at approximately 25 degrees even after exiting the patient's vein. Accordingly, the stiffness-varying IV needle 110 is non-reusable and it is possible to prevent an accident, such as medical staff being sticked by the stiffness-varying IV needle 110.

To this end, the body member 111 may be manufactured using at least one of a liquid metal having a melting point lower than the body temperature range, a liquid metal-based composite material, and a heat-responsive variable-stiffness polymer. For example, the liquid metal may include gallium (Ga) and a melting point of gallium is about 29.76 degrees. In this case, at room temperature, for example, at approximately 25 degrees, gallium is in a solid state and has a high stiffness of about 9.8 GPa. Therefore, the stiffness-varying IV needle 110 may be maintained in a rigid form. Meanwhile, after the stiffness-varying IV needle 110 is inserted into the patient' vein, gallium may be liquefied in the body temperature range, for example, approximately 37 degrees, and the stiffness-varying IV needle 110 may be maintained in the soft form. In addition, after exiting the patient's vein, gallium does not change back to the solid state at room temperature, for example, at approximately 25 degrees, due to a supercooling phenomenon as illustrated in FIG. 3, and the stiffness-varying IV needle 110 may be maintained in the soft form. In detail, while gallium converts to a liquid state at a melting point, much lower temperature than an actual melting point is required due to the supercooling phenomenon to convert back the melted gallium to the solid state through a cooling process. As a result of experiments, gallium in the liquid state did not convert to the solid state even when gallium was cooled at the temperature of approximately 5 degrees Celsius and converted to the solid state at the very low temperature of approximately-5 degrees Celsius.

In an example embodiment, as illustrated in FIG. 1, the body member 111 may include two half-body members. Each of the half-body members may extend in a longitudinal direction of the body member 111 and may have the same shape. The half-body members may implement the body member 111 by coupling to each other in a direction perpendicular to the longitudinal direction with the channel 113 therebetween. In another example embodiment, the body member 111 may be implemented in an integrated, completely hollow cylindrical shape. In this case, the body member 111 may be implemented as an integrated body member using molding technology or thermal drawing.

The channel 113 may be formed on the inner surface of the body member 111 and may provide a passage 114 for the drug inside the body member 111. The channel 113 may be formed of a biocompatible material. For example, the biocompatible material may include a biocompatible polymer, for example, a silicone polymer. Therefore, the drug may contact the channel 113 without contacting the body member 111. In some example embodiments, the passage 114 may have a square or circular cross-sectional outline shape. Therefore, a cross section of the body member 111 may be a frame structure around the channel 113, that is, the passage 114.

The coating member 115 may cover the outer surface of the body member 111. The coating member 115 may be formed of a biocompatible material. For example, the biocompatible material may include a biocompatible polymer, for example, a silicone polymer. For example, the silicone polymer may include RT623 having a high tear strength greater than 30 N/mm. Therefore, the patient's biological tissue may contact the coating member 115 without contacting the body member 111.

In an example embodiment, as illustrated in FIG. 1, the coating member 115 may include two half-coating members. The half-coating members may each extend along a longitudinal direction of the coating member 115 and may have the same shape or different shapes. The half-coating members may implement the coating member 115 by coupling to each other in a direction perpendicular to the longitudinal direction with the body member 111 therebetween. In another example embodiment, the coating member 115 may be implemented in an integrated, complete shape. In some example embodiments, the coating member 115 may include a plurality of coating layers. In this case, the coating member 115 may include the plurality of coating layers, for example, a silicone polymer and Parylene.

The temperature sensor 116 may be provided between the body member 111 and the coating member 115. Here, the temperature sensor 116 may be in a thin film form, more specifically, a nano thin film form. The temperature sensor 116 may be provided along the direction of the elongated body member 111, in such a manner that the sensing part of the temperature sensor 116 is placed near the sharp tip end of the stiffness-varying IV needle 110 that is inserted into the vein. In some example embodiments, when the coating member 115 includes the plurality of coating layers, the temperature sensor 116 may be provided between the coating layers as illustrated in FIG. 2A. Also, the temperature sensor 116 may have a curved shape and accordingly, may be smoothly and seamlessly joined between the body member 111 and the coating member 115. Therefore, the temperature sensor 116 may operate without contacting the patient's biological tissue. The temperature sensor 116 may be used to monitor the patient's core body temperature while the stiffness-varying IV needle 110 is inserted into the patient's vein. Consequently, the temperature sensor 116 may be used to detect undesired drug leakage that may occur when the stiffness-varying IV needle 110 is inserted at an erroneous location within the soft biological tissue. In this manner, the temperature sensor 116 does not necessitate a medical device required to monitor the patient's condition or a drug injection state and enables a better medical service to be provided to the patient.

In an example embodiment, as illustrated in (a) of FIG. 4, the temperature sensor 116 may include a first protective layer 117, a sensing layer 118, and a second protective layer 119. The first protective layer 117 may support the sensing layer 118 and the second protective layer 119. The first protective layer 117 may be attached to the body member 111 or one of the coating layers of the coating member 115. Here, the first protective layer 117 may be formed of a polymer material, for example, polyethylene terephthalate (PET). The sensing layer 118 may be driven to actually sense temperature. Here, the sensing layer 118 may be formed of a metal material, for example, gold (Au). The second protective layer 119 may cover and protect all of the first protective layer 117 and the sensing layer 118 on the sensing layer 118. The second protective layer 119 may be attached to the coating member 115 or one of the coating layers of the coating member 115. Here, the second protective layer 119 may be formed of a polymer material, for example, polydimethylsiloxane (PDMS). For example, the first protective layer 117, the sensing layer 118, and the second protective layer 119 may have thicknesses of 3.6 μm, 180 nm, and 10 μm, respectively. In this case, as illustrated in (b) of FIG. 4, in the temperature sensor 116, that is, the sensing layer 118, a resistance changes in response to temperature according to a predetermined resistance change rate. Therefore, temperature may be sensed from the temperature sensor 116 based on the resistance change.

Figure 5:
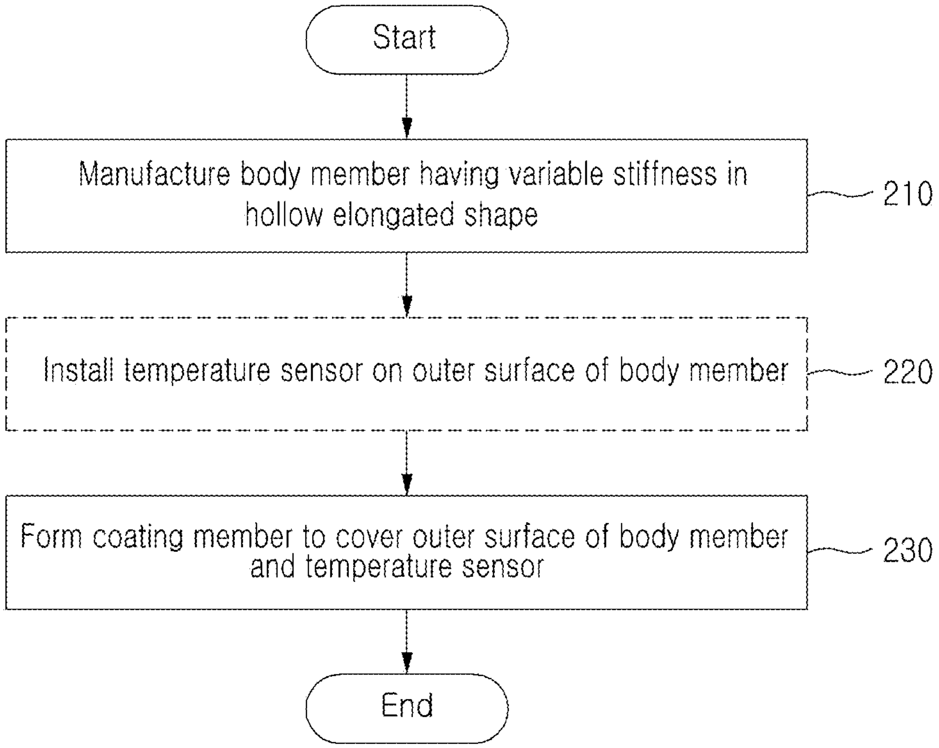
FIG. 5 is a flowchart illustrating a method of manufacturing a stiffness-varying IV needle according to various example embodiments.

FIG. 5 is a flowchart illustrating a method of manufacturing the stiffness-varying IV needle 110 according to various example embodiments.

Referring to FIG. 5, in operation 210, the body member 111 may be manufactured. The body member 111 may be implemented in a hollow elongated shape through which drug passes. In some example embodiments, the body member 111 may have a square or circular cross-sectional outline shape. The body member 111 may have a variable stiffness according to ambient temperature. That is, the body member 111 may have a stiffness that may vary in response to ambient temperature. To this end, the body member 111 may be manufactured using at least one of a liquid metal having a melting point lower than the body temperature range, a liquid metal-based composite material, and a heat-responsive variable-stiffness polymer. For example, the liquid metal may include gallium (Ga) and a melting point of gallium is about 29.76 degrees Celsius.

In an example embodiment, as illustrated in FIG. 1, the body member 111 may include two half-body members. Each of the half-body members may extend in a longitudinal direction of the body member 111 and may have the same shape. The half-body members may implement the body member 111 by coupling to each other in a direction perpendicular to the longitudinal direction with the channel 113 therebetween. In another example embodiment, the body member 111 may be implemented in an integrated, completely hollow cylindrical shape. In this case, the body member 111 may be implemented as an integrated body member using molding technology or thermal drawing.

In a first example embodiment, after the channel 113 is formed, the body member 111 may be formed around the channel 113. The channel 113 may provide the passage 114 for the drug and may be formed of a biocompatible material. For example, the biocompatible material may include a biocompatible polymer, for example, a silicone polymer. For example, the passage 114 may have a square or circular cross-sectional outline shape. Therefore, a cross section of the body member 111 may be a frame structure around the channel 113, that is, the passage 114.

In operation 220, the temperature sensor 116 may be formed on the outer surface of the body member 111. Here, the temperature sensor 116 may be in a thin film form, more specifically, a nano thin film form. The temperature sensor 116 may be provided adjacent near the sharp tip end of the body member 111. Also, the temperature sensor 116 may have a serpentine shape and accordingly, may be seamlessly and smoothly coupled on the outer surface of the body member 111. In some example embodiments, operation 220 may be excluded. That is, the temperature sensor 116 may not be installed on the outer surface of the body member 111 and operation 230 may be performed.

In operation 230, the coating member 115 may be formed to cover the outer surface of the body member 111 and the temperature sensor 116. The coating member 115 may be formed of a biocompatible material. For example, the biocompatible material may include a biocompatible polymer, for example, a silicone polymer. For example, the silicone polymer may include RT623 having a high tear strength greater than 30 N/mm.

In an example embodiment, as illustrated in FIG. 1, the coating member 115 may include two half-coating members. The half-coating members may each extend along the longitudinal direction of the coating member 115 and may have the same shape or different shapes. The half-coating members may implement the coating member 115 by coupling to each other in a direction perpendicular to the longitudinal direction with the body member 111 therebetween. In another example embodiment, the coating member 115 may be implemented in an integrated, complete shape around the body member 111. In some example embodiments, the coating member 115 may include a plurality of coating layers. In this case, the coating member 115 may include the plurality of coating layers, for example, a silicone polymer and Parylene.

In some example embodiments, some of the coating layers of the coating member 115 may be formed to cover the outer surface of the body member 111 and, after the temperature sensor 116 is installed on the formed coating layers, remaining coating layers of the coating member 115 may be formed to cover the formed coating layers and the temperature sensor 116.

In a second example embodiment, when manufacturing the body member 111, the channel 113 may not be formed and, instead, the channel 113 and the coating member 115 may be formed together. In an example embodiment, the channel 113 and the coating member 115 may be separately formed. For example, in the case of using molding technology, the channel 113 and the coating member 115 may be separately formed. In another example embodiment, the body member 111 and the channel 113 and the coating member 115 may be simultaneously formed. For example, in the case of using thermal drawing technology, the body member 111 and the channel 113 and the coating member 115 may be simultaneously formed.

In this manner, the stiffness-varying IV needle 110 may be manufactured.

Figure 6:
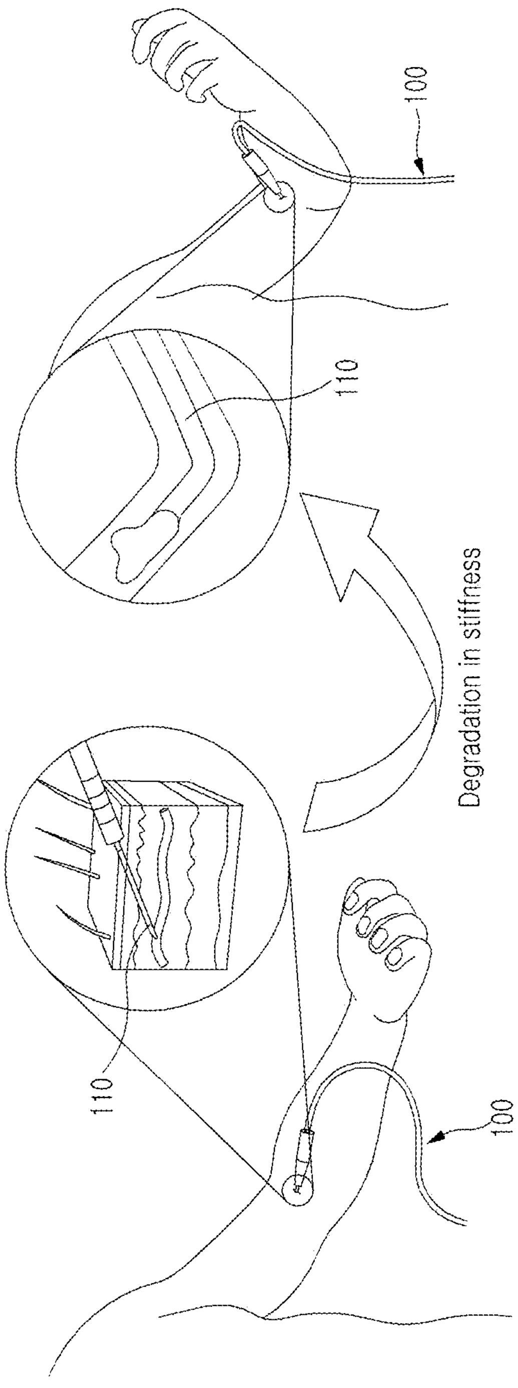
FIG. 6 illustrates an example of using a stiffness-varying IV needle according to various example embodiments.

FIG. 6 illustrates an example of using the stiffness-varying IV needle 110 according to various example embodiments.

Referring to FIG. 6, the stiffness-varying IV needle 110 may be manufactured with high stiffness for maintaining a predefined shape at temperature below a body temperature range and thus, may be maintained with the corresponding stiffness while ambient temperature is below the body temperature range. Therefore, as illustrated on the left of FIG. 6, the stiffness-varying IV needle 110 may be maintained in a rigid form at room temperature, for example, at approximately 25 degrees and thus, may be inserted into the patient's vein. If the ambient temperature changes to be greater than or equal to the body temperature range, the stiffness-varying IV needle 110 may change to have a lower stiffness than the corresponding stiffness and become flexible, making the shape deformable. Therefore, after insertion into the patient's vein, the stiffness-varying IV needle 110 may be maintained in a soft form in the body temperature range, for example, at approximately 37 degrees Celsius. Therefore, as illustrated on the right of FIG. 6, the stiffness-varying IV needle 110 may be deformed inside the patient's vein that follows the movement of biological tissue around a location at which the stiffness-varying IV needle 110 is inserted. This allows stable and continuous drug delivery without damaging the blood vessel wall while the stiffness-varying IV needle 110 is inserted into the patient' vein. Here, a maximum flow rate of the stiffness-varying IV needle 110 may be 39.92 mL/min±1.84 mL/min. That is, the IV needle 110 may exhibit improved bio-tissue affinity.

To compare performance between the conventional metal needle and IV catheter and the stiffness-varying IV needle 110, experiments were performed using artificial biological tissue with a stiffness of about 415 kPa. Conventional metal needle and the IV catheter generally have the stiffness of 200 GPa and 400 MPa, respectively, and thus, were easily inserted into the blood vessel within the artificial biological tissue. However, when a movement or a deformation occurred in the artificial biological tissue after insertion, the conventional metal needle and IV catheter damaged the blood vessel wall. On the contrary, the stiffness-varying IV needle 110, in its rigid form, was easily inserted into the blood vessel within the artificial biological tissue like the conventional metal needle and IV catheter, but converted from the rigid form to a soft form after insertion and deformed to match a movement or a deformation of the artificial biological tissue. As a result, the blood vessel wall was not damaged.

Meanwhile, to compare the performance between the conventional IV catheter and the stiffness-varying IV needle 110, experiments were performed on artificial blood vessels with various radii of curvature. As a result, the conventional 18G IV catheter having a size similar to a size of the stiffness-varying IV needle 110 failed in injecting drug with a radius of curvature of 1 mm. On the contrary, the stiffness-varying IV needle 110 stably injected the drug not only in a straight line but also with up to a radius of curvature of 5 mm and succeeded in injecting the drug without damaging the blood vessel wall even with the radius of curvature of 1 mm.

In addition, once the ambient temperature changes to be greater than or equal to the body temperature range, the stiffness-varying IV needle 110 may be maintained at a low stiffness without returning to an original stiffness although the ambient temperature changes back to be below the body temperature range. Therefore, the stiffness-varying IV needle 110 may be maintained in a soft form at room temperature, for example, at approximately 25 degrees even after exiting the patient's vein. Accordingly, the stiffness-varying IV needle 110 is non-reusable and it is possible to prevent an accident, such as medical staff being sticked by the stiffness-varying IV needle 110.

Figure 7:
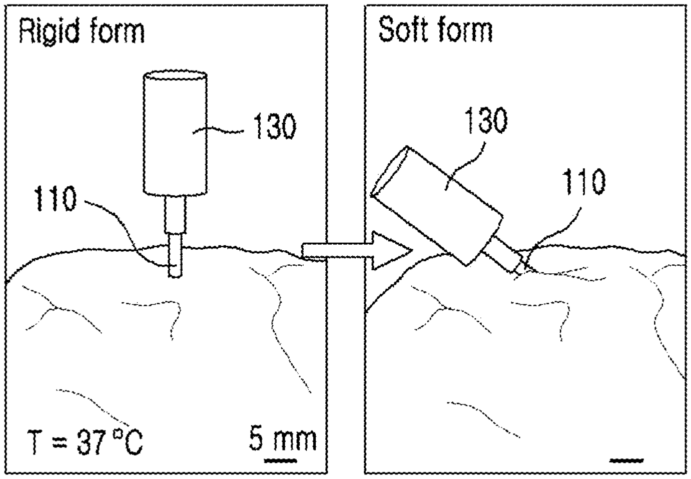
FIG. 7 illustrates an example of explaining a change of a stiffness-varying IV needle in a biological tissue according to various example embodiments.
Figure 7:
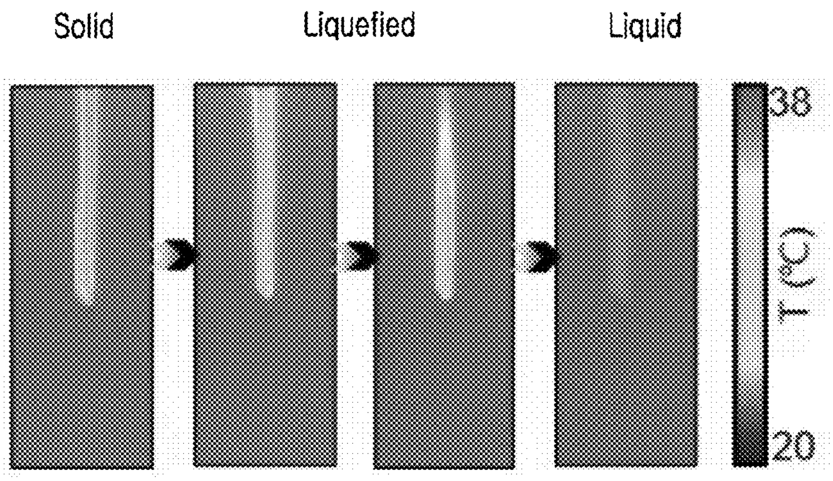

FIG. 7 illustrates an example of explaining a change in a biological tissue of the stiffness-varying IV needle 110 according to various example embodiments.

Referring to FIG. 7, while the stiffness-varying IV needle 110 is inserted into the biological tissue, the stiffness-varying IV needle 110 may convert from a rigid form to a soft form. To verify this, experiments were performed using the biological tissue of a pig at approximately 37 degrees Celsius. Here, the body member 111 of the stiffness-varying IV needle 110 was manufactured using gallium. In detail, as illustrated in (a) of FIG. 7, the stiffness-varying IV needle 110 was inserted into the biological tissue of the pig in a rigid form and, as a result, converted from the rigid form to a soft form within the biological tissue of the pig. Here, as illustrated in (b) of FIG. 7, the body member 111 within the stiffness-varying IV needle 110 was liquefied and changed from a solid state to a liquid state. Therefore, as the body member 111 is liquefied, the stiffness-varying IV needle 110 may convert to the soft form and be deformable to match a movement or a deformation of the biological tissue.

Figure 8:
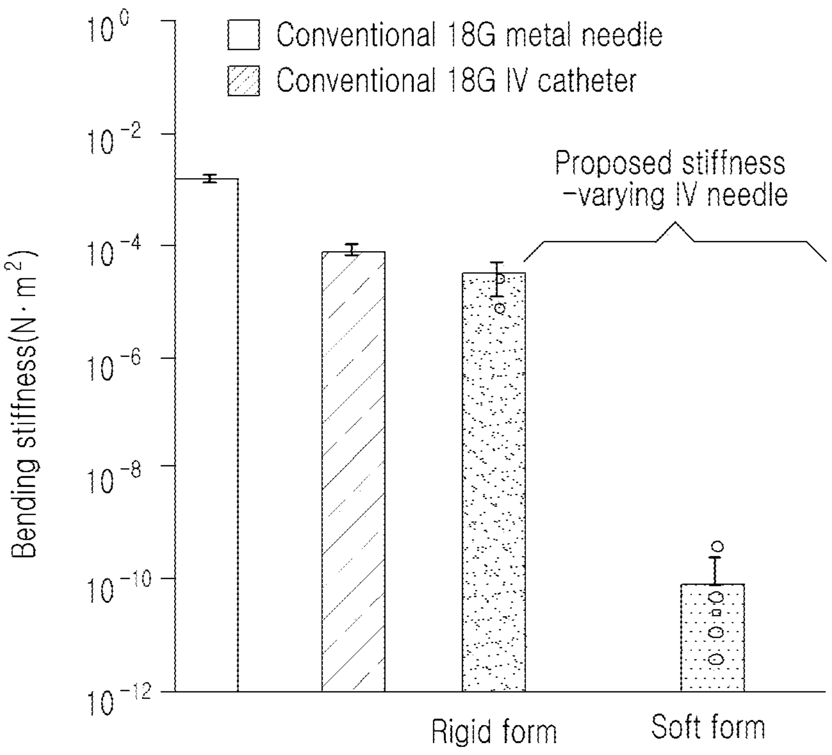
FIG. 8 is a graph explaining a bending stiffness of a stiffness-varying IV needle according to various example embodiments.

FIG. 8 is a graph explaining a bending stiffness of the stiffness-varying IV needle 110 according to various example embodiments.

Referring to FIG. 8, in response to conversion of the stiffness-varying IV needle 110 from a rigid form to a soft form, a bending stiffness of the stiffness-varying IV needle 110 may vary. To verify this, a bending stiffness in the rigid form and a bending stiffness in the soft form were measured for the stiffness-varying IV needle 110. As a result, when in the rigid form, the stiffness-varying IV needle 110 exhibited a bending stiffness similar to that of the conventional 18G IV catheter (e.g., $2.99\times10^{-5}$ N·m$^2$). Meanwhile, when in the soft form, the stiffness-varying IV needle 110 exhibited a significantly reduced bending stiffness (e.g., $8.77\times10^{-11}$ N·m$^2$). Here, a rate of change of the bending stiffness according to the stiffness-varying IV needle 110 converting from the rigid form to the soft form exceeded $10^5$ times. Therefore, the stiffness-varying IV needle 110 may be inserted into the vein in the rigid form and deformable along the vein in the soft form.

Figure 9:
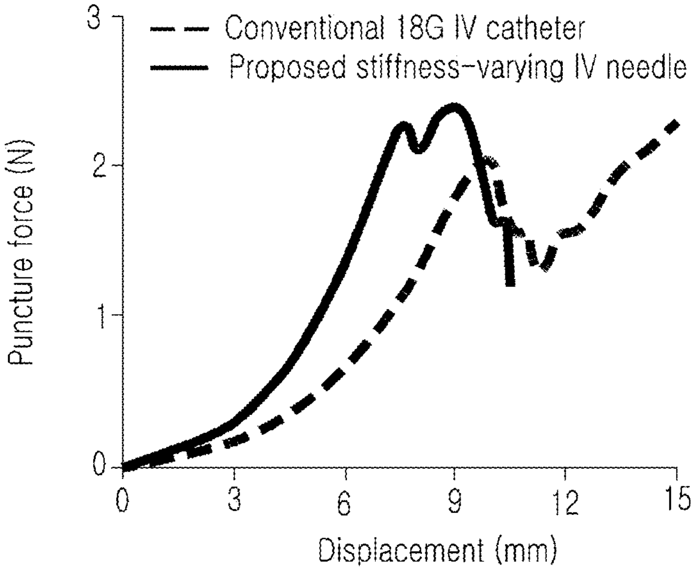
FIG. 9 is a graph explaining a puncture force of a stiffness-varying IV needle according to various example embodiments.

FIG. 9 is a graph explaining a puncture force of the stiffness-varying IV needle 110 according to various example embodiments.

Referring to FIG. 9, the stiffness-varying IV needle 110 may have a sufficient puncture force to insert into the biological tissue in a rigid form. To verify this, the puncture force of the stiffness-varying IV needle 110 was measured using the artificial biological tissue with a stiffness of about 415 kPa that mimics the stiffness of the vein, that is, approximately 200 to 600 kPa. In detail, the stiffness-varying IV needle 110 was inserted into the artificial biological tissue and then removed and was not bent in this process. When in the rigid form, the stiffness-varying IV needle 110 exhibited a puncture force similar to that of the conventional 18G IV catheter. As described above, the stiffness-varying IV needle 110 has a sufficient stiffness to be inserted into the vein in the rigid form.

Additionally, to verify biocompatibility of the stiffness-varying IV needle 110, a change in weight of a laboratory mouse was observed by inserting samples of stiffness-varying IV needle 110 and the conventional metal needle and IV catheter into the right leg of the laboratory mouse. When the stiffness-varying IV needle 110 was inserted, a highest weight gain was observed after 14 days, confirming high biocompatibility. Similar to a comparison group when the conventional metal needle and IV catheter were inserted, a rate of change in the weight of each of biological organs did not significantly change, confirming that there is no effect of reducing the biocompatibility by the coating member 150 of the stiffness-varying IV needle 110. When a liver function value (alanine aminotransferase (ALT)) and muscle damage-related values (aspartate transaminase (AST) and lactate dehydrogenase (LDH)) were compared to the comparison group, it was confirmed that the stiffness-varying IV needle 110 reduced values due to the softening effect, which represents the high biomechanical compatibility of the stiffness-varying IV needle 110. Considering that metabolism-related values (TG, TC, GLU) and a kidney function value (BUN) are also at similar levels, the stiffness-varying IV needle 110 has biocompatibility and thus, does not have adverse effect on a specific biological organ or metabolism. Even when activity of immune cells (i.e., neutrophil, eosinophil, macrophage) was measured, the stiffness-varying IV needle 110 showed much lower values than the conventional metal needle due to its flexibility, indicating that there is less risk of causing an inflammatory reaction. Through haematoxylin-eosin (H & E) and terminal deoxynucleotidyl transferase dUTP nick end labeling (TUNEL) tests, it was verified that the stiffness-varying IV needle 110 produces fewest infiltering cells and minimizes inflammatory reaction compared to the conventional metal needle and IV catheter.

Additionally, CYP2E1 (cytochrome P450 2E1) reactivity was measured by connecting the IV infusion set 100 to inferior vena cava (IVC) and then flowing ethylene glycol tetraacetic acid (EGTA) into a liver. A result similar to reactivity when using the conventional IV catheter was obtained and it was verified that the developed stiffness-varying IV needle 110 successfully delivered the drug in a soft state in vivo. As a result of comparing the degree of stains between H&E and CYP2E1 by observing a cross section of the liver, similar results were actually shown when using the conventional IV catheter and the stiffness-varying IV needle 110, which made it confirmed that the drug delivery ability of the stiffness-varying IV needle 110 is similar to a commercial product.

Figure 10:
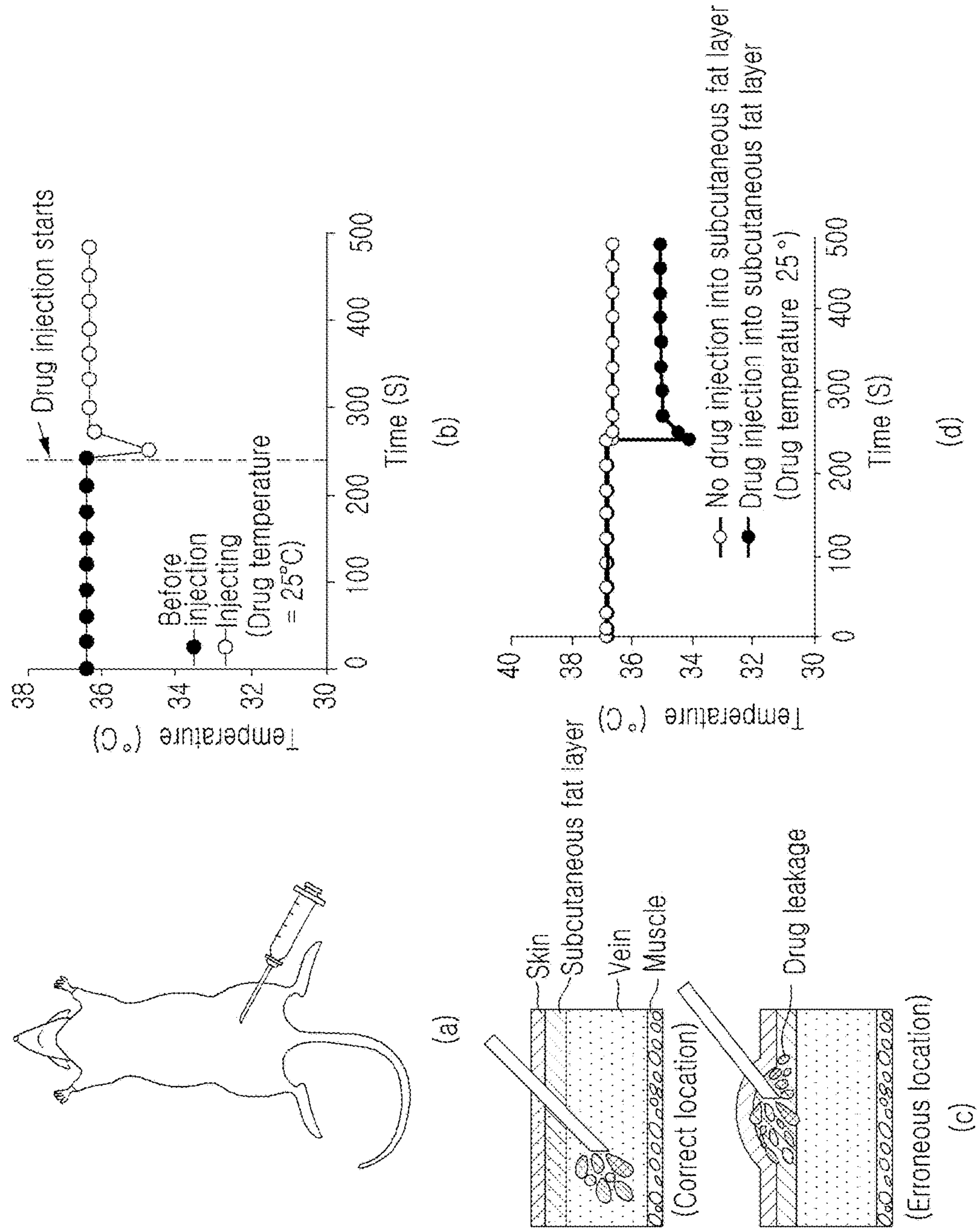
FIG. 10 illustrates an example of using a temperature sensor in a stiffness-varying IV needle according to various example embodiments.

FIG. 10 illustrates an example of using the temperature sensor 116 in the stiffness-varying IV needle 110 according to various example embodiments.

As illustrated in (a) of FIG. 10, it was verified that whether to inject a drug may be determined by measuring body temperature through the temperature sensor 116 of the stiffness-varying IV needle 110 when phosphate buffered saline (PBS) at 25 degrees Celsius was flowed into the abdomen of a mouse using the stiffness-varying IV needle 110. That is, when the stiffness-varying IV needle 110 was accurately inserted into the vein as illustrated in an upper portion of (c) of FIG. 10, the stiffness-varying IV needle 110 did not exhibit a great difference in temperature before or after drug injection due to blood flow as illustrated in (b) of FIG. 10. However, when the drug is injected by inserting the stiffness-varying IV needle 110 at an erroneous location within the soft biological tissue (i.e., a subcutaneous fat layer outside the blood vessel, not inside the blood vessel) as illustrated in a lower portion of (c) of FIG. 10, temperature of the tissue significantly drops due to drug leakage as illustrated in (d) of FIG. 10. Therefore, whether the drug injection is normally performed may be verified by monitoring body temperature using the stiffness-varying IV needle 110 having the temperature sensor 116.

According to example embodiments, the stiffness-varying IV needle 110 may be maintained in a rigid form at room temperature due to its variable stiffness after being manufactured and may be inserted into a patient's vein and, after insertion into the vein, may convert to a soft form in a body temperature range and be deformable along the patient's vein. Therefore, the stiffness-varying IV needle 110 may continue to stably inject a drug without damaging the blood vessel wall while being inserted into the patient's vein. Here, since the stiffness-varying IV needle 110 irreversibly converts its stiffness in the body temperature range and is maintained in a soft form at room temperature even after exiting the patient's vein, its reuse is impossible and it is possible to prevent an accident, such as medical staff being sticked by the stiffness-varying IV needle 110.

Also, according to example embodiments, since the stiffness-varying IV needle 110 includes the temperature sensor 116, the temperature sensor 116 may be used to monitor the patient's core body temperature while the stiffness-varying IV needle 110 is inserted into the patient's vein. Conversely, the temperature sensor 116 may be used to detect undesired drug leakage that may occur when the stiffness-varying IV needle 110 is inserted at an erroneous location within the soft biological tissue. In this manner, the temperature sensor 116 does not necessitate a medical device required to monitor the patient's condition or a drug injection state and enables a better medical service to be provided to the patient.

Therefore, the stiffness-varying IV needle 110 may minimize damage to the blood vessel and inflammation during an IV infusion process and, after its use, may prevent a sticking accident or a risk of reuse by the stiffness-varying IV needle 110 and accordingly, may be widely used in medical fields that require IV infusion. The stiffness-varying IV needle 110 may lead the growing needle-related market in line with the increasing number of IV infusion treatments. The conventional IV catheter has high marketability, but has some issues, such as a sticking wound or inflammation due to a high stiffness during its use. The stiffness-varying IV needle 110 capable of being flexible may fundamentally solve the issues, such as damage to the blood vessel and inflammation caused by the high stiffness, a sticking accident after its use, and syringe reuse, which are found in the conventional metal needle and IV catheter, and accordingly, may have high competitiveness in the medical syringe market. The stiffness-varying IV needle 110 has a size and a puncture force similar to those of the conventional IV catheter and accordingly, is easily replaceable and becomes flexible within 1 minute after insertion. Therefore, the stiffness-varying IV needle 110 is expected to improve the stability of IV infusion. The stiffness-varying IV needle 110 is manufactured to prevent damage to the blood vessel wall due to a movement of a patient by achieving a similar a mechanical stiffness to that of the venous blood vessel through softening and to be unable to return to its previous state of having a puncture force once it is softened. Therefore, the probability of reuse during a disposal process is eliminated. The temperature of an injection site or the patient's condition or drug injection state may be easily monitored using the temperature sensor 116 attached at the sharp tip end of the stiffness-varying IV needle 110, which is expected to revolutionize the field of IV infusion treatment. The stiffness-varying IV needle 110 may meet all the requirements emphasized by the WHO, non-reusable and safely usable needles, and thus, is expected to have very high usability.

Example embodiments provide the stiffness-varying IV needle 110 that converts to a soft form by body temperature and has a temperature sensing function, the IV infusion set 100 having the same, and the manufacturing method thereof.

The stiffness-varying IV needle 110 disclosed herein may include the body member 111 implemented in a hollow elongated shape through which fluid passes and having a variable stiffness according to ambient temperature; and the coating member 115 configured to cover the outer surface of the body member 111 and having biocompatibility.

According to some example embodiments, the fluid can be such as but not limited to the following: pharmacological agents, nutrients, or therapeutic drugs.

According to various example embodiments, the body member 111 may be manufactured with a high stiffness to maintain a predefined shape at temperature below a body temperature range and maintained at the stiffness while the ambient temperature is below the body temperature range, and if the ambient temperature changes to be greater than or equal to the body temperature range, the body member 111 may change to have a lower stiffness than the previous stiffness, making the shape deformable.

According to various example embodiments, the body member 111 may be maintained at the lower stiffness although the ambient temperature greater than or equal to the body temperature range changes back to be below the body temperature range.

According to various example embodiments, the body member 111 may be manufactured using at least one of a liquid metal having a melting point lower than a body temperature range, a liquid metal-based composite material, and a heat-responsive variable-stiffness polymer.

According to various example embodiments, the liquid metal may include gallium.

According to various example embodiments, the coating member 115 may include a biocompatible polymer, or may include a plurality of coating layers consisting of a silicone polymer and Parylene.

According to various example embodiments, the stiffness-varying IV needle 110 may further include the thin film-typed temperature sensor 116 provided between the body member 111 and the coating member 115.

According to various example embodiments, the stiffness-varying IV needle 110 may further include the channel 113 formed on the inner surface of the body member 111, configured to provide the passage 114 for the fluid inside the body member 111, and having biocompatibility.

According to various example embodiments, each of the passage 114 and the body member 111 may have a square or circular cross-sectional outline shape.

According to various example embodiments, the body member 111 may include two half-body members that are implemented as the body member 111 by coupling to each other in a direction perpendicular to a longitudinal direction.

According to some example embodiments, the passage 114 and the body member 111 may have a circular cross-sectional outline shape and may be implemented as an integrated cylindrical hollow body member using molding technology or thermal drawing.

The IV infusion set 100 disclosed herein may include the stiffness-varying IV needle 110, the tube 120 through which fluid is supplied, and the hub 130 fastened between the stiffness-varying IV needle 110 and the tube 120 and configured to allow the stiffness-varying IV needle 110 and the tube 120 to communicate and to provide the fluid supplied through the tube 120 to the stiffness-varying IV needle 110. The stiffness-varying IV needle 110 may include the body member 111 implemented in a hollow elongated shape through which the fluid passes and having a variable stiffness according to ambient temperature; and the coating member 115 configured to cover the outer surface of the body member 111 and having biocompatibility.

According to some example embodiments, the fluid can be such as but not limited to the following: pharmacological agents, nutrients, or therapeutic drugs.

According to various example embodiments, the body member 111 may be manufactured with a high stiffness to maintain a shape predefined at temperature below a body temperature range and maintained at the stiffness while the ambient temperature is below the body temperature range, and if the ambient temperature changes to be greater than or equal to the body temperature range, the body member may change to have a lower stiffness than the previous stiffness, making the shape deformable.

According to various example embodiments, the body member 111 may be maintained at the lower stiffness although the ambient temperature changes back to be below the body temperature range.

According to various example embodiments, the stiffness-varying IV needle 110 may further include the thin film-typed temperature sensor 116 provided between the body member 111 and the coating member 115.

According to various example embodiments, the stiffness-varying IV needle 110 may further include the channel 113 formed on the inner surface of the body member 111 to provide the passage 114 for the fluid inside the body member 111, and having biocompatibility.

The method of manufacturing the stiffness-varying IV needle 110 disclosed herein may include operation 210 of manufacturing the body member 111 having a variable stiffness according to ambient temperature to be implemented in a hollow elongated shape through which fluid passes; and operation 230 forming the coating member 115 having biocompatibility to cover the outer surface of the body member 111.

According to some example embodiments, the fluid can be such as but not limited to the following: pharmacological agents, nutrients, or therapeutic drugs.

According to various example embodiments, operation 210 of manufacturing the body member 111 may include manufacturing the body member 111 using at least one of a liquid metal having a melting point lower than a body temperature range, a liquid metal-based composite material, and a heat-responsive variable-stiffness polymer.

According to various example embodiments, operation 230 of forming the coating member 115 may include operation 220 of installing the thin film-typed temperature sensor 116 on the outer surface of the body member 111; and operation 230 of forming the coating member 115 to cover the outer surface of the body member 111 and the temperature sensor 116.

According to an example embodiment, operation 210 of manufacturing the body member 111 may include forming the channel 113 configured to provide the passage 114 for the fluid and having biocompatibility; and forming the body member 111 around the channel 113.

According to another example embodiment, the method of manufacturing the stiffness-varying IV needle 110 may further include forming the channel 113 configured to provide the passage 114 for the fluid inside the body member 111 and having biocompatibility, and the forming of the channel 113 and the forming of the coating member 115 may be separately performed or simultaneously performed.

According to an example embodiment, operation 210 of manufacturing the body member 111 may include manufacturing the two half-body members and forming the body member 111 by coupling the half-body members in a direction perpendicular to a longitudinal direction.

According to another example embodiment, operation 210 of manufacturing the body member 111 may include forming an integrated, cylindrical hollow body member 111.

Various example embodiments and the terms used herein are not construed to limit description disclosed herein to a specific implementation and should be understood to include various modifications, equivalents, and/or substitutions of a corresponding example embodiment. In the drawings, like reference numerals refer to like components throughout the present specification. The singular forms "a," "an," and "the" are intended to include the plural forms as well, unless the context clearly indicates otherwise. Herein, the expressions, "A or B," "at least one of A and/or B," "A, B, or C," "at least one of A, B, and/or C," and the like may include any possible combinations of listed items. Terms "first," "second," etc., are used to describe corresponding components regardless of order or importance and the terms are simply used to distinguish one component from another component. The components should not be limited by the terms. When a component (e.g., a first component) is described to be "(functionally or communicatively) connected to" or "accessed to" another component (e.g., a second component), the component may be directly connected to the other component or may be connected through still another component (e.g., a third component).

According to various example embodiments, each of the components may include a singular object or a plurality of objects. According to various example embodiments, at least one of the components or operations may be omitted. Alternatively, at least one another component or operation may be added. Alternatively or additionally, a plurality of components may be integrated into a single component. In this case, the integrated component may perform one or more functions of each of the components in the same or similar manner as it is performed by a corresponding component before integration. According to various example embodiments, operations performed by a module, a program, or another component may be performed in a sequential, parallel, iterative, or heuristic manner. Alternatively, at least one of the operations may be performed in different sequence or omitted. Alternatively, at least one another operation may be added.

Although the example embodiments are described with reference to some specific example embodiments and accompanying drawings, it will be apparent to one of ordinary skill in the art that various alterations and modifications in form and details may be made in these example embodiments without departing from the spirit and scope of the claims and their equivalents. For example, suitable results may be achieved if the described techniques are performed in different order, and/or if components in a described system, architecture, device, or circuit are combined in a different manner, and/or replaced or supplemented by other components or their equivalents.

Therefore, other implementations, other example embodiments, and equivalents of the claims are to be construed as being included in the claims.

What is claimed is:

1. A stiffness-varying intravenous (IV) needle comprising:

a body member implemented in a hollow elongated shape through which fluid passes and having a variable stiffness according to ambient temperature; and a coating member configured to cover the outer surface of the body member and having biocompatibility, wherein the body member is manufactured using a liquid metal having a melting point lower than a body temperature range, the liquid metal including gallium.

2. The stiffness-varying IV needle of claim 1, wherein the body member is manufactured with a high stiffness to maintain a predefined shape at temperature below a body temperature range and maintained at the stiffness while the ambient temperature is below the body temperature range, and if the ambient temperature changes to be greater than or equal to the body temperature range, the body member changes to have a lower stiffness than the previous stiffness, making the shape deformable.

3. The stiffness-varying IV needle of claim 2, wherein the body member is maintained at the lower stiffness although the ambient temperature greater than or equal to the body temperature range changes back to be below the body temperature range.

4. The stiffness-varying IV needle of claim 1, wherein the coating member includes a biocompatible polymer, or includes a plurality of coating layers consisting of a silicone polymer and Parylene.

5. The stiffness-varying IV needle of claim 1, further comprising:

a thin film-typed temperature sensor provided between the body member and the coating member.

6. The stiffness-varying IV needle of claim 1, further comprising:

a channel formed on the inner surface of the body member, configured to provide a passage for the fluid inside the body member, and having biocompatibility.

7. The stiffness-varying IV needle of claim 6, wherein each of the passage and the body member has a square or circular cross-sectional outline shape, and the body member includes two half-body members that are implemented as the body member by coupling to each other in a direction perpendicular to a longitudinal direction.

8. The stiffness-varying IV needle of claim 1, wherein the body member has a circular cross-sectional outline shape and is implemented as an integrated cylindrical hollow body member using molding technology or thermal drawing.

9. An intravenous (IV) infusion set comprising:

a stiffness-varying IV needle;

a tube through which fluid is supplied; and a hub fastened between the stiffness-varying IV needle and the tube and configured to allow the stiffness-varying IV needle and the tube to communicate and to provide the fluid supplied through the tube to the stiffness-varying IV needle, wherein the stiffness-varying IV needle comprises:

a body member implemented in a hollow elongated shape through which the fluid passes and having a variable stiffness according to ambient temperature; and a coating member configured to cover the outer surface of the body member and having biocompatibility, wherein the body member is manufactured with a high stiffness to maintain a shape predefined at temperature below a body temperature range and maintained at the stiffness while the ambient temperature is below the body temperature range, and if the ambient temperature changes to be greater than or equal to the body temperature range, the body member changes to have a lower stiffness than the previous stiffness, making the shape deformable, wherein the body member is maintained at the lower stiffness although the ambient temperature greater than or equal to the body temperature range changes back to be below the body temperature range.

10. The IV infusion set of claim 9, wherein the stiffness-varying IV needle further comprises a thin film-typed temperature sensor provided between the body member and the coating member.

11. The IV infusion set of claim 9, wherein the stiffness-varying IV needle further comprises a channel formed on an inner surface of the body member, configured to provide a passage for the fluid inside the body member, and having biocompatibility.

* * * * *